United States Patent [19]

Schuettler et al.

[11] Patent Number: 5,362,492
[45] Date of Patent: Nov. 8, 1994

[54] METHOD OF INHIBITING MULTIPLE ORGAN FAILURE IN TRAUMA PATIENTS BY ADMINISTRATION OF SUPEROXIDE DISMUTASE

[75] Inventors: Achim Schuettler, Aachen; Leopold Flohé, Roetgen; Volker Buehren; Ingo Marzi, both of Homburg/Saar, all of Germany; Otmar Trentz, Zurich, Switzerland

[73] Assignee: Gruenenthal GmbH, Stohlberg/Rhld., Germany

[21] Appl. No.: 21,722

[22] Filed: Feb. 25, 1993

Related U.S. Application Data

[63] Continuation of Ser. No. 797,188, Nov. 25, 1991, abandoned.

[30] Foreign Application Priority Data

Dec. 4, 1990 [DE] Germany ............... 4038563

[51] Int. Cl.$^5$ ............. A61K 37/50; A61K 37/02
[52] U.S. Cl. ............. 424/94.4; 514/2; 435/189
[58] Field of Search ............. 424/94.4; 435/189; 514/2

[56] References Cited

U.S. PATENT DOCUMENTS

| | | | |
|---|---|---|---|
| 3,637,640 | 1/1972 | Huber | 530/401 |
| 4,952,409 | 8/1990 | Bando et al. | 424/450 |
| 4,976,959 | 12/1990 | Berger, Jr. et al. | 424/94.4 |
| 5,080,886 | 1/1992 | Mickle et al. | 424/94.4 |
| 5,080,894 | 1/1992 | Hunter et al. | 424/94.4 |
| 5,091,180 | 2/1992 | Walker et al. | 514/568 |
| 5,116,616 | 5/1992 | Gonenne | 424/94.4 |
| 5,130,245 | 7/1992 | Marklund et al. | 435/189 |
| 5,171,680 | 12/1992 | Mullenbach et al. | 424/94.4 |
| 5,180,582 | 1/1993 | Maeda et al. | 424/94.4 |
| 5,223,538 | 6/1993 | Fridovich et al. | 424/94.64 |
| 5,227,405 | 7/1993 | Fridovich et al. | 424/94.64 |

FOREIGN PATENT DOCUMENTS

| | | |
|---|---|---|
| 19477 | 11/1980 | European Pat. Off. . |
| 138111 | 4/1985 | European Pat. Off. . |
| 172577 | 2/1986 | European Pat. Off. . |
| 180964 | 5/1986 | European Pat. Off. . |
| 189182 | 7/1986 | European Pat. Off. . |
| 213628 | 3/1987 | European Pat. Off. . |
| 283244 | 9/1988 | European Pat. Off. . |
| 284105 | 9/1988 | European Pat. Off. . |
| 295826 | 12/1988 | European Pat. Off. . |
| 342620 | 11/1989 | European Pat. Off. . |
| 266504 | 4/1989 | German Dem. Rep. . |
| 1924230 | 7/1970 | Germany . |
| 2259404 | 6/1973 | Germany . |
| 2259405 | 6/1973 | Germany . |
| 3715662 | 5/1987 | Germany . |
| 3639725 | 7/1987 | Germany . |
| WO87/01387 | 3/1987 | WIPO . |

OTHER PUBLICATIONS

Muramoto et al., "Therapeutic Effects of Superoxide Dismutase . . . ", *Free Radical Biol. Med.*, 9, (Suppl. 1):144, (1990).

Suzuki et al., *Amer. J. Physiol.*, 257:H1740–H1745 (Nov. 1989).

Schlag, et al., *Circulatory Shock*, vol. 31, Abstract No. 8 (1990).

McCord et al., "Superoxide Dismutase", *The Journal of Biological Chemistry*, vol. 244, No. 22, (1969), pp. 6049–6055.

Steffens et al., "The Primary Structure of Cu-Zn Superoxide Dimutase from Photobacterium leiognathi:

(List continued on next page.)

*Primary Examiner*—Stephen G. Walsh
*Attorney, Agent, or Firm*—Evanson, McKeown, Edwards & Lenahan

[57] ABSTRACT

The use of superoxide dismutases for the prevention and/or treatment of organ failure in patients at risk with polytrauma caused by accidents is disclosed. The superoxide dismutases are administered according to the invention in daily doses of from 1 g to 15 g for a period of at least two days following the initial trauma (i.e. the accident), especially by intravenous infusion. Preferably natural or recombinant human copper/zinc superoxide dismutase is used.

10 Claims, 1 Drawing Sheet

OTHER PUBLICATIONS

Evidence for a Separate Evolution of Cu-Zn Superoxide Dismutase in Bacteria", *Hoppe-Seyler's Z. Physiol. Chem.*, BD, 364, S. 675-690 (1983).

Greenspan et al., "Abbreviated Injury Scale and Injury Severity Score: A Scoring Chart", *The Journal of Trauma*, vol. 25, No. 1, pp. 60-64 (1985).

Goris et al., "Multiple-Organ Failure", *Arch Surg.*, vol. 120, pp. 1109-1115 (1985).

Kreinhoff et al., *Infusionstherapie*, vol. 17, pp. 261-267 (1990), summary only.

Chan et al., *Advances in Neurology*, vol. 52, pp. 177-183 (1990).

Kufterin et al., *Patol Fiziol Eksp Ter*, (1), pp. 17-19 (Jan.-Feb. 1990), abstract only.

Kufterin et al., *Patol Fiziol Eksp Ter*, (6) pp. 44-46 (Nov.-Dec. 1989), abstract only.

Michelson et al., *Free Rad. Res. Commun.*, vol. 4, pp. 209-224 (1988).

Chan et al., *Annals of Neurology*, vol. 21, pp. 540-547 (1987).

Naftchi et al., *Peptides*, vol. 3, pp. 235-247 (1982).

Patent Abstracts of Japan, C-166, May 18, 1983, vol. 7, No. 114, abstract of Yabuki, Japanese Patent Application No. JP 56-130012.

Faist et al., "Multiple Organ Failure in Polytrauma Patients", *The Journal of Trauma*, vol. 23, No. 9, pp. 775-787 (1983).

Civetta et al., "Critical Care", Lippincott, Philadelphia, (1988), pp. 1569-1573.

Schneider et al., "Effects of Recombinant Human Superoxide Dismutase on Increased Lung Vascular Permeability and Respiratory Disorder in Endotoxemic Rats", *Circulatory Shock*, vol. 30, pp. 97-106 (1990).

Schneeberger et al., "Prevention of Acute Renal Failure After Kidney Transplantation by Treatment with rh-SOD . . . ", *Transplantation Proceedings*, vol. 22, pp. 2224-2225 (1990).

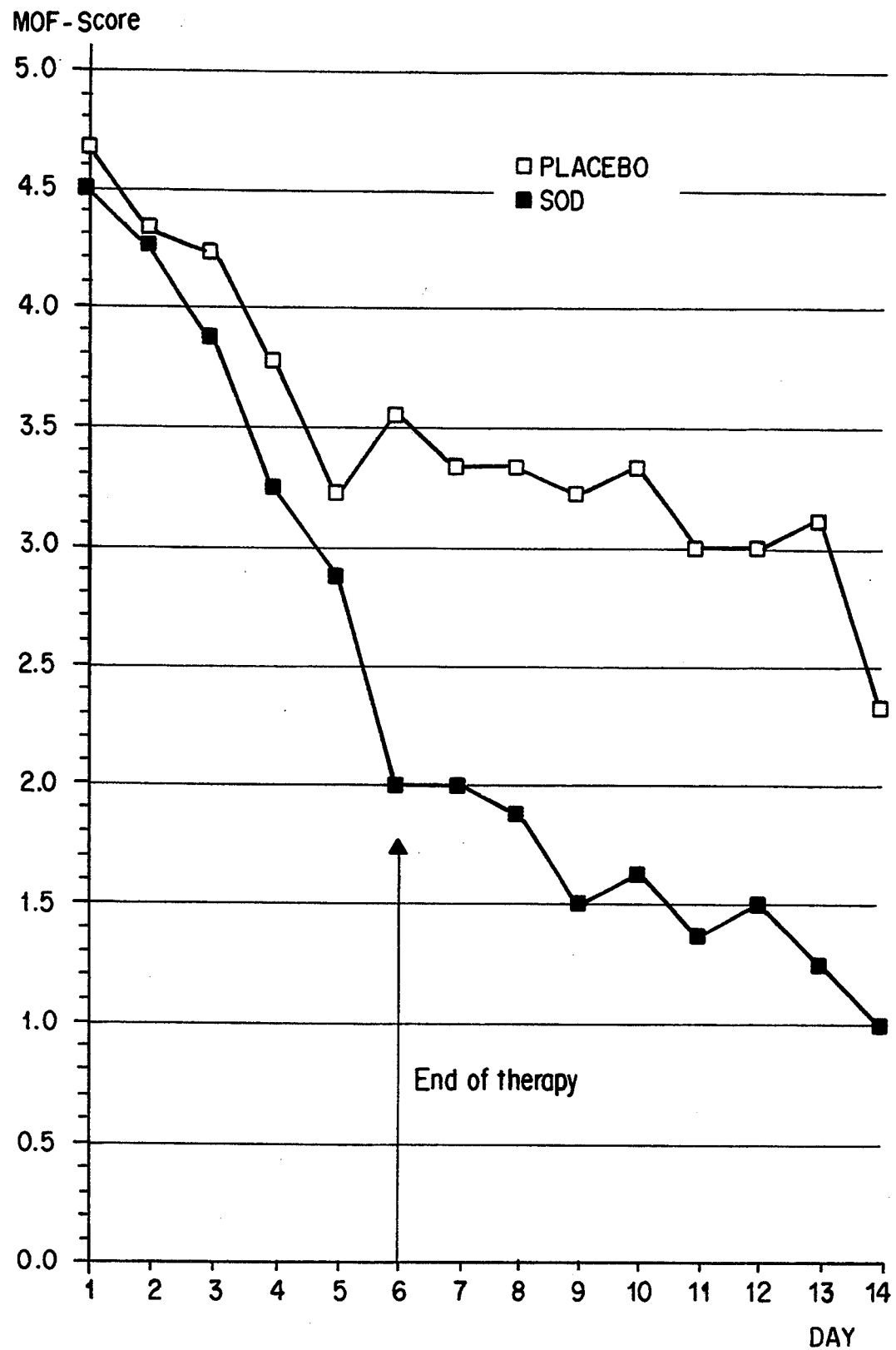

METHOD OF INHIBITING MULTIPLE ORGAN FAILURE IN TRAUMA PATIENTS BY ADMINISTRATION OF SUPEROXIDE DISMUTASE

This application is a continuation of application Ser. No. 07/797,188, filed Nov. 25, 1991, now abandoned.

BACKGROUND OF THE INVENTION

The present invention relates to the use of superoxide dismutases for the prevention and/or treatment of organ failure in patients with polytrauma caused by accidents.

Multiple organ failure is the major cause of death in patients suffering from polytrauma caused by an accident who survive the first 24 hours after surgical treatment. The mechanisms which lead to this life-threatening complication are still mostly obscure. Consequently, it has not been possible in the past to devise a specific treatment or method of preventing of this life-threatening complication.

The clinical signs of sepsis and subsequent organ failure are attributed almost exclusively to the invasion of bacteria and the liberation of endotoxins. It has been suggested that the activation of the complement system by endotoxins is the initial event which subsequently leads to the formation of numerous deleterious mediators, such as oxygen radicals. Despite remarkable progress in basic research on septic shock, it remains unclear what importance is attributable to the effects of oxygen radicals in comparison with other mediators. In several animal studies of sepsis models like endotoxin shock, it could be demonstrated that treatment with superoxide dismutase exhibited some efficacy in relation to the course of the syndrome and to the survival rate.

However, this approach was not effective in experimental trauma models either in rats or in primates (Circ. Shock 31, abstr. no. 8; 1990), and it was consequently widely thought that oxygen radicals probably did not play an important role in the arena of mediators after this event.

SUMMARY OF THE INVENTION

It is the object of the present invention to provide a method for the prevention and/or treatment of organ failure in patients at risk of multiple organ failure.

It is also an object of the present invention to provide a method of treating a patient suffering from polytrauma caused by an accident.

These and other objects of the invention are achieved by providing a method of inhibiting organ failure in a polytrauma patient at risk thereof, said method comprising administering to said patient an effective organ failure inhibiting amount of superoxide dismutase.

BRIEF DESCRIPTION OF THE DRAWING

The invention will be described in further detail with reference to the accompanying drawing FIGURE, which is a graph of the average multiple organ failure scores of a group of patients treated with superoxide dismutase according to the invention and of a control group.

DETAILED DESCRIPTION OF PREFERRED EMBODIMENTS

Surprisingly, it has now been observed in clinical studies that treatment of patients suffering from polytrauma caused by an accident with high doses of superoxide dismutase is of significant benefit with respect to avoiding the development of life-threatening posttraumatic complications including multiple organ failure. Moreover no side effects result from administering even high doses of superoxide dismutase for several days. This observed benefit may result from the fact that the multiple injuries from a polytrauma and their consequences may be defined as a repeated reperfusion injury (which is known to be a source of oxygen radicals).

Superoxide dismutases are naturally occurring metallo-proteins which dismutate superoxide radicals to the less toxic hydrogen peroxide. Generally these enzymes contain one or two metal cations such as the cations of iron, manganese, copper, zinc, cadmium, cobalt and/or mercury. Like most other mammalian superoxide dismutases, the human enzyme contains a combination of copper and zinc. The human copper/zinc-superoxide dismutase consists of two identical subunits of 153 amino acid residues, each of which contains one copper and one zinc atom. It is a dimeric enzyme with a molecular weight of 32,000 Daltons. A high molecular weight copper/zinc-superoxide dismutase of eucaryotic origin has also been described which is a tetrameric molecule having a molecular weight of 130,000 Daltons. Manganese superoxide dismutase of eucaryotic origin is a tetrameric molecule with a molecular weight of 80,000 Daltons, whereas the iron and manganese forms of superoxide dismutases of bacterial origin are dimeric and have molecular weights of about 40,000 Daltons.

Many processes for preparing superoxide dismutases are known in the art. For instance, the isolation of superoxide dismutase from erythrocytes, liver or other human or mammalian tissues has been described in German patent No. DE 1,924,230; German patent No. 2,259,405, published German patent application No. DE 2,259,404; and published European patent application No. EP 19,477. In human superoxide dismutase the N-terminus is acetylated, but superoxide dismutases from a number of other natural sources do not contain such N-acetyl groups.

Alternatively superoxide dismutases may also be obtained from cultivated transformed cell lines as described in published international patent application No. WO 87/01,387. The preparation of superoxide dismutases using transformed bacteria or yeasts is described in published German patent application No. DE 3,639,725; published European patent application No. EP 172,577; published European patent application No. EP 284,105; European patent No. EP 180 964, and elsewhere.

Processes for the preparation of superoxide dismutases in yeasts using recombinant DNA-techniques are described in published European patent application No. EP 138,111; and published European patent application No. EP 213,628. The process described in published European patent application No. EP 138,111 produces human superoxide dismutase in which the N-terminus is acetylated.

The copper/zinc superoxide dismutase used in the clinical studies described hereinafter was prepared in transformed yeast cells according to the procedure disclosed in published European patent application No. EP 138,111. It has a minimum specific activity of 3 000 U/mg, as determined by the method described in J. Biol. Chem. 244, 6049–6055 (1969). Its amino acid sequence is identical to that of copper/zinc superoxide dismutase of native human origin described, e.g., in Hoppe-Seyler, Z. Physiol. Chem. 364, 675–690 (1983).

Pharmaceutical preparations containing superoxide dismutases as active ingredients for use in therapeutic applications other than polytrauma or multiple organ failure have been described in U.S. Pat. No. 3,637,640; published European patent application No. EP 172,577; published European patent application No. 295,826; and published European patent application No. EP 342,620. Each of these prior superoxide dismutase preparations may also be used in the method of the present invention for treating polytrauma and/or preventing multiple organ failure.

In the use of the method of the invention for preventing and/or treating organ failure comprising administering superoxide dismutase to a patient who is suffering from polytrauma caused by an accident and who consequently is at risk of multiple organ failure, the superoxide dismutase generally is administered to the patient by intravenous infusion in an amount providing constant and sufficiently high plasma levels over a period of several days starting as soon as possible after the accident or the primary surgical care. To achieve such plasma levels, the dosage generally should range from about 1 g to about 15 g per day. Such dosages are generally sufficient to produce plasma levels ranging from about 30,000 units to about 100,000 units of superoxide dismutase per liter of plasma. Preferably, from about 2 g to about 8 g of superoxide dismutase per day is administered to the patient.

The preferred pharmaceutical form for parenteral administration is a sterile, pyrogen-free superoxide dismutase preparation obtained by lyophilization.

The duration of the infusion therapy will necessarily depend on the particular situation of the patient and is within the discretion of the treating physician. In general, however, it is reasonable to treat a patient for a period of at least 2 days ranging up to about 10 days.

The surprising significant benefit with regard to inhibiting the development of post-traumatic life-threatening complications, including single or multiple organ failure, obtainable by infusion of superoxide dismutase to patients suffering from polytrauma caused by an accident was demonstrated in a clinical study performed as follows:

Twenty-four patients of either sex were included in a randomized, placebo-controlled, double-blind clinical trial in parallel groups. The inclusion criteria were:

Polytrauma patients with an "injury severity score" (ISS) of $\geq 27$ [c.f. Greenspan et al., J. Trauma 25, 60–64 (1985)];

Age more than 18 years;

Treatment according to invention initiated not later than 48 hours after the initial trauma event (i.e. the accident).

The patients suffered from multiple fractures and/or severe soft tissue injuries due to accidents which had occurred in traffic or in the work place. Patients with major head trauma as the predominant injury were excluded.

Infusion therapy with superoxide dismutase was started as soon as possible after the primary surgical care. The infusion rate of superoxide dismutase was 3 g per day, and the duration of the infusion period was 5 days. The patients were followed up in the study until day 14, and clinical and biochemical parameters were continuously monitored. The monitoring of clinical and biochemical parameters was primarily focussed on those parameters needed for the evaluation of the "multiple organ failure score" (MOF score) according to Goris et al., Arch. Surg. 120, 1109–1115 (1985). In addition, several special biochemical parameters were determined which may be of interest in elucidating the unknown underlying mechanisms of post-traumatic organ failure, such as e.g. the plasma levels of elastase.

Recently, it has been shown that the plasma level of granulocyte elastase correlates with the incidence of post-injury complications in polytrauma patients, see Deutsches Arzteblatt 87, 952–956 (1990). An elastase level of 85 $\mu$g/l on the 5th day after the traumatic event is described as a discrimination point above which there is a very high incidence of the development of severe complications including organ failure.

In the present study the elastase values on day 6 (which is the 5th day after the initial trauma) were 57.9±5.7 $\mu$g/l for the group treated with superoxide dismutase. For the placebo group the elastase values were 112±23.7 $\mu$g/l. The numbers of patients with elastase levels below or above the discrimination point of 85 $\mu$g/l on day 1 and day 6 are shown in the following table:

| Treatment | Elastase Levels | | | |
|---|---|---|---|---|
| | Day 1 | | Day 6 | |
| | <85 $\mu$g/l | >85 $\mu$g/l | <85 $\mu$g/l | >85 $\mu$g/l |
| Superoxide Dismutase | 1 | 11 | 11 | 1* |
| Placebo | 2 | 10 | 5 | 7 |

*patient with Elastase level of 86 $\mu$g/l

As can be seen from the table, by day six the elastase level in all but one of the patients treated with superoxide dismutase had decreased to less than the critical value of 85 $\mu$g/l, and the elastase level in the one exception was only 86 $\mu$g/l.

A similar difference was found in the acute phase C-reactive protein which was 104±16 mg/ml in the group treated with superoxide dismutase and 160±19 mg/ml in the placebo group.

The general clinical evaluation of the severity of posttraumatic complications defined by the multiple organ failure score (MOF score) according to Goris et al., supra. is also in agreement with the laboratory data.

The evaluation of the MOF scores clearly indicates a significant benefit for the patients treated with superoxide dismutase compared with the placebo group. This benefit can be easily seen in the accompanying FIG. 1, which is a comparative graph of the MOF scores of the group of patients treated with superoxide dismutase (SOD) (indicated by solid squares) and those of the control (Placebo) group (indicated by hollow squares). The lower values of the MOF-Score indicate a better organ function.

The results of the clinical study show that the use of superoxide dismutase according to the present invention in the treatment of patients suffering from polytrauma caused by an accident provides a significant benefit with respect to inhibiting the development of posttraumatic complications, including multiple organ failure, in such patients. In other words, administration of superoxide dismutase in accordance with the invention to polytrauma patients significantly decreases the likelihood that complications such as multiple organ failure will occur.

The foregoing description has been set forth merely to illustrate and exemplify the invention and is not intended to limit its scope. Since modifications of the described embodiments incorporating the spirit and substance of the invention may occur to persons skilled in the art, the scope of the invention should be limited solely with respect to the appended claims and equivalents.

What is claimed is:

1. A method of inhibiting multiple organ failure in a patient at risk thereof suffering from polytrauma caused by an accident wherein brain trauma as predominant injury is excluded, said method comprising administering to said patient an effective multiple organ failure inhibiting amount of superoxide dismutase.

2. A method according to claim 1, wherein a dosage in the range from about 1 to about 15 grams of superoxide dismutase per day is administered to the patient.

3. A method according to claim 2, wherein a dosage in the range from about 2 to about 8 grams of superoxide dismutase per day is administered to the patient.

4. A method according to claim 1, wherein superoxide dismutase is administered for a period of 5 to 10 days after the patient initially suffers the trauma.

5. A method according to claim 1, wherein said superoxide dismutase is administered by intravenous infusion.

6. A method according to claim 1, wherein said superoxide dismutase is natural or recombinant human copper/zinc superoxide dismutase.

7. A method according to claim 1, wherein an amount of superoxide dismutase is administered to the patient sufficient to continuously maintain the level of superoxide dismutase in the patient's blood plasma in the range from about 30,000 units to about 100,000 units of superoxide dismutase per liter of plasma.

8. A method according to claim 7, wherein said superoxide dismutase is administered by intravenous infusion.

9. A method according to claim 1, wherein about 3 grams of human copper/zinc superoxide dismutase per day are administered to said patient by intravenous infusion for a period of about 5 days.

10. In a method of treating a patient suffering from multiple organ failure due to polytrauma caused by an accident wherein brain trauma as predominant injury is excluded, the improvement comprising administering to said patient an effective multiple organ failure inhibiting amount of superoxide dismutase.

* * * * *